(12) United States Patent
Moore et al.

(10) Patent No.: US 8,772,335 B2
(45) Date of Patent: Jul. 8, 2014

(54) ADAMANTYL DERIVATIVES AS THERAPEUTIC AGENTS

(71) Applicant: Women & Infants' Hospital of Rhode Island, Providence, RI (US)

(72) Inventors: Richard G. Moore, Cranston, RI (US); Rakesh K. Singh, Barrington, RI (US)

(73) Assignee: Woman & Infants' Hospital of Rhode Island, Providence, RI (US)

( * ) Notice: Subject to any disclaimer, the term of this patent is extended or adjusted under 35 U.S.C. 154(b) by 0 days.

(21) Appl. No.: 13/706,958

(22) Filed: Dec. 6, 2012

(65) Prior Publication Data

US 2013/0143962 A1 Jun. 6, 2013

Related U.S. Application Data

(60) Provisional application No. 61/567,223, filed on Dec. 6, 2011.

(51) Int. Cl.
| | | |
|---|---|---|
| *A01N 37/00* | (2006.01) | |
| *A61K 31/21* | (2006.01) | |
| *A61K 31/27* | (2006.01) | |
| *C07C 331/20* | (2006.01) | |
| *A61K 45/06* | (2006.01) | |
| *C07C 333/20* | (2006.01) | |
| *A61K 31/26* | (2006.01) | |

(52) U.S. Cl.
CPC .............. *C07C 333/20* (2013.01); *A61K 31/27* (2013.01); *C07C 2103/74* (2013.01); *C07C 331/20* (2013.01); *A61K 45/06* (2013.01); *A61K 31/26* (2013.01)
USPC ...................................................... 514/513

(58) Field of Classification Search
None
See application file for complete search history.

(56) References Cited

U.S. PATENT DOCUMENTS 3,929,806 A * 12/1975 Schmid et al. ................. 546/292
7,842,835 B2 * 11/2010 Kozikowski et al. ........... 564/32

OTHER PUBLICATIONS

Bianchini et al. "Isothiocyanates in Cancer Prevention." *Drug Metab. Rev.* 36.3-4(2004):655-667.
Fahey et al. "The Chemical Diversity and Distribution of Glucosinolates and Isothiocyanates Among Plants." *Phytochem.* 56.1(2001):5-51.
Hidgon et al. "Cruciferous Vegetables and Human Cancer Risk: Epidemiologic Evidence and Mechanistic Basis." *Pharmacol. Res.* 55.3(2007):224-236.
Lange et al. "Cytotoxic Properties of Adamantyl Isothiocyanate and Potential In vivo Metabolite Adamantyl-N-Acetylcystein in Gynecological Cancer Cells." *Chem. Biol. Drug Des.* 79(2012):92-103.
Singh et al. "A Novel Indole Ethyl Isothiocyanate (7Me-IEITC) with Anti-Proliferative and Pro-Apoptotic Effects on Platinum-Resistant Human Ovarian Cancer Cells." *Gynecol. Oncol.* 109.2(2008):240-249.
Singh et al. "Effect of Indole Ethyl Isothiocyanates on Proliferation, Apoptosis, and MAPK Signaling in Neuroblastoma Cell Lines." *Bioorg. Med. Chem. Lett.* 17.21(2007):5846-5852.
Singh et al. "Isothiocyanate NB7M Causes Selective Cytotoxicity, Pro-Apoptotic Signalling and Cell-Cycle Regression in Ovarian Cancer Cells." *Br. J. Cancer.* 99.11(2008):1823-1831.

* cited by examiner

*Primary Examiner* — Craig Ricci
*Assistant Examiner* — Jared D Barsky
(74) *Attorney, Agent, or Firm* — Mintz Levin Cohn Ferris Glovsky and Popeo, P.C.; Ingrid A. Beattie

(57) ABSTRACT

The present invention relates to adamantyl derivatives and their anti-cancer activity. Compounds of formulae I and II are provided as well as related methods of treatment and methods of synthesis.

2 Claims, 12 Drawing Sheets

Log$_{10}$ AC-AM concentration [M]

A
Synthesis

Adamantyl-Isothiocyanate
(ITC-AM)

Adamantyl-N-acetylcystein
(AC-AM)

Reaction conditions:
(a) Thiophosgene, 20% NaHCO3 (aq), EtOAC, 4 h 80% yield  (b) N-acetylcysteine, EtOH, H2O, 48 h 85% yield B
*In-vivo* conversion

ADAMANTYL DERIVATIVES AS THERAPEUTIC AGENTS

CROSS REFERENCE TO RELATED APPLICATIONS

This application claims benefit of U.S. Provisional Application Ser. No. 61/567,223, filed Dec. 6, 2011, the contents of which are incorporated herein by reference.

FIELD OF THE INVENTION

The invention is related to novel adamantyl derivatives and their use as therapeutic agents for one or more diseases, such as cancer.

BACKGROUND OF THE INVENTION

Recently many studies have reported that Indole ethyl isothiocyanates (Singh et al, *British journal of cancer*, 2008, 99:1823-1831; Gynecologic Oncology, 2008, 109:240-249; Bioorg and Med Chem Lett 2007, 17:5846-5852) inhibited the growth of ovarian, neuroblastoma, prostate, pancreatic, and breast cancer cells in culture by inducing apoptosis. Phenyl ethyl isothiocyanate (PEITC) has been shown to induce apoptotic cell death in HeLa cells in a time- and concentration-dependent manner, through rapid and transient induction of caspase-3-like activity and activation of JNKs. The involvement of caspases, including caspase-3 and caspase-8, and JNKs in phenyl ethyl isothiocyanate (PEITC) induced apoptosis has also been established in other cell lines including human leukemia HL-60 cells. PEITC induces apoptosis potently in a p53-deficient PC-3 human prostate cancer cell line mediated by ERKs.

The anti-carcinogenic potential of isothiocyanates (ITCs) are demonstrated further by the finding that their metabolites formed in vivo possess similar, if not more potent, anticarcinogenic activity in cultured cells or animal models. ITCs are rapidly metabolized mainly through the mercapturic acid pathway in both humans and animals, giving rise to various dithiocarbamate metabolites, such as cysteinyl glycine, cysteine, and N-acetylcysteine conjugates which are excreted in the urine.

SUMMARY OF THE INVENTION

It has now been discovered that a number of adamantyl derivatives display anticancer activity. This has been demonstrated in vitro in various cultured solid tumor cancer cells such as neuroblastoma, breast, ovarian, endometrial, prostate, pancreatic, vulvar, liver and in other non-solid human tumors as well.

One aspect of this invention includes compounds having the formula (I) or (II):

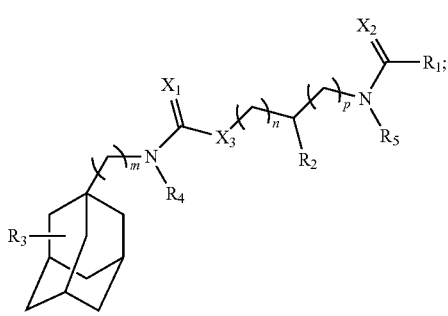

(I)

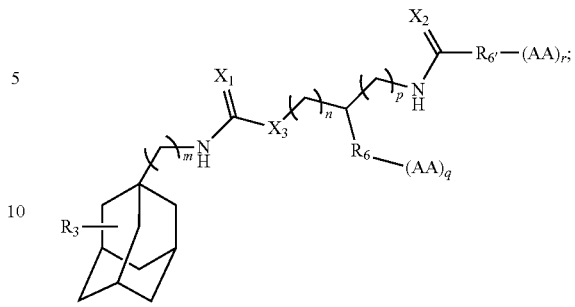

(II)

wherein $X_1$, $X_2$ and $X_3$ are each, independently, O, S, $NR_x$ or $CR_7R_{7'}$;

m, n and p are each, independently, integers from 0 to 20;

q and r are each, independently, integers from 1 to 20;

$R_1$, $R_2$ and $R_3$ are each, independently, hydrogen, nitro, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, unsubstituted or substituted $C_{2-8}$ alkynyl, hydroxyl, halogen, —$NR_{10}R_{11}$, —$C(O)R_{10}$, —$C(O)OR_{10}$, —$NR_{11}C(O)R_{10}$, —$C(O)NR_{10}R_{11}$, —$OC(O)R_{10}$, —$NR_{11}C(S)R_{10}$, or —$SO_2R_{12}$;

$R_4$ and $R_5$ are each, independently, hydrogen or unsubstituted or substituted $C_1$-$C_8$ alkyl;

$R_6$ and $R_{6'}$ are each, independently, a bond, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, unsubstituted or substituted $C_2$-$C_8$ alkynyl, —$NR_{14}$—, —$C(O)$— or —$SO_2$—;

$R_x$ is hydrogen, unsubstituted or substituted $C_1$-$C_8$ alkyl, or —$NR_yR_z$;

$R_y$ and $R_z$ are each, independently, hydrogen, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, or unsubstituted or substituted $C_2$-$C_8$ alkynyl;

$R_7$ and $R_{7'}$ are each, independently, hydrogen, nitro, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, unsubstituted or substituted $C_2$-$C_8$ alkynyl, hydroxyl, halogen, —$NR_8R_9$, —$C(O)R_8$, —$C(O)OR_8$, —$NR_9C(O)R_8$, —$C(O)NR_8R_9$, —$OC(O)R_8$, —$NR_9C(S)R_8$, or —$SO_2R_{15}$;

$R_8$, $R_9$, $R_{10}$ and $R_{11}$ are each, independently, hydrogen, hydroxyl, unsubstituted or substituted $C_1$-$C_8$ alkoxyl, unsubstituted or substituted $C_1$-$C_8$ alkyl, —$NR_{13}R_{13'}$, or —$NR_{14}NR_{13}R_{13'}$;

$R_{12}$ and $R_{15}$ are each, independently, halogen, hydroxyl, —$NR_{15}R_{15'}$, —$P(O)(OR_{15})_3$, CN, or —$NR_{17}NR_{16}R_{16'}$;

$R_{14}$ and $R_{17}$ are each, independently, hydrogen or unsubstituted or substituted $C_1$-$C_8$ alkyl;

$R_{13}$, $R_{13'}$, $R_{15}$, $R_{15'}$, $R_{16}$ and $R_{16'}$ are each, independently, hydrogen, hydroxyl, or unsubstituted or substituted $C_1$-$C_8$ alkyl; and each AA is, independently, a substituted or unsubstituted, naturally occurring or synthetic amino acid;

or a pharmaceutically acceptable salt, prodrug, tautomer, regioisomer, stereoisomer, diastereomer, enantiomer or racemate thereof.

An exemplary compound has the following formula/structure:

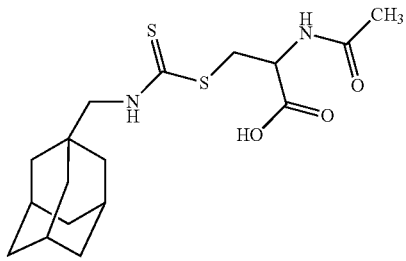 [SMILES: CC(=O)NC(CSC(=S)NCC12CC3CC(CC(C3)C1)C2)C(=O)O]

Another aspect of the present invention provides pharmaceutical compositions comprising a therapeutically effective amount of a compound described herein and a pharmaceutically acceptable carrier.

Further, one aspect of the present invention provides methods for treating cancer in a subject in need of such treatment, the method comprising administering to the subject a therapeutically effective amount of a compound described herein or a combination of compounds described herein. In one embodiment, methods described herein may combine with a therapeutically effective amount of at least one additional therapeutically active agent against cancer.

For example, the present invention provides methods for treating cancer, such as neuroblastoma, ovarian cancer, breast cancer, cervical cancer, endometrial cancer, prostate cancer, pancreatic cancer, vulvar cancer, liver cancer, colorectal cancer, lymphoma, leukemia and others.

Objects of the present invention will be appreciated by those of ordinary skill in the art from a reading of the Figures and the detailed description of the preferred embodiments which follow, such description being merely illustrative of the present invention.

A method of synthesizing a compound of the invention is also provided herein. Such a method of synthesis comprises:
(a) mixing adamantyl methyl amine in a solvent;
(b) reacting the mixture of step (a) with thiophosgene and collecting the resultant product;
(c) reacting the product from step (b) with an amino acid in the presence of sodium bicarbonate; and
(d) extracting the product of step (c).

A method for treating cancer in a subject in need of such treatment is carried out by administering to the subject a therapeutically effective amount of one or more of the compounds described herein. In preferred embodiments, the cancer comprises a gynecological cancer such as an ovarian cancer or an endometrial cancer. Some patients with gynecological cancers develop recurrent disease, and in turn, may develop platinum- and/or multidrug-resistant tumors. For example, chemoresistant tumors do not respond or respond poorly to standard chemo treatment such as platinum-based drugs like carboplatin and paclitaxel. The compounds described herein are particularly useful in treatment of such chemoresistant tumors. Optionally, the methods further comprise administering to the subject an inhibitor of a pro-survival factor, an inhibitor of a growth factor (e.g., epidermal growth factor (EGF)), or a redox-modulating agent.

The following abbreviations appear in the specification: AC-AM, adamantyl-N-acetylcystein; FACS, fluorescent-activated cell sorting; ITC, isothiocyanate; ITC-AM (or AMITC), adamantyl iso-thiocyanate; MAPK, mitogen-activated protein kinase; and ROS, reactive oxygen species.

The compounds described for therapeutic use are purified. Purity is measured by any appropriate standard method, for example, by column chromatography, thin layer chromatography, or high-performance liquid chromatography (HPLC) analysis. "Purified" also defines a degree of sterility that is safe for administration to a human subject, e.g., lacking infectious or toxic agents. For example, a purified compound is one that is at least 90%, 91%, 92%, 93%, 94%, 95%, 98%, 99%, or 100% (w/w) of the composition by weight.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

FIG. 10 (B) shows in vivo drug conversion. Phytochemical dietary isothiocyanate (ITC) in the human body is converted to N-acetylcysteine conjugates (N-AC). N-AC is converted in vivo to ITC or is disposed of through urinary excretion.

DETAILED DESCRIPTION OF THE INVENTION

Figure 1:
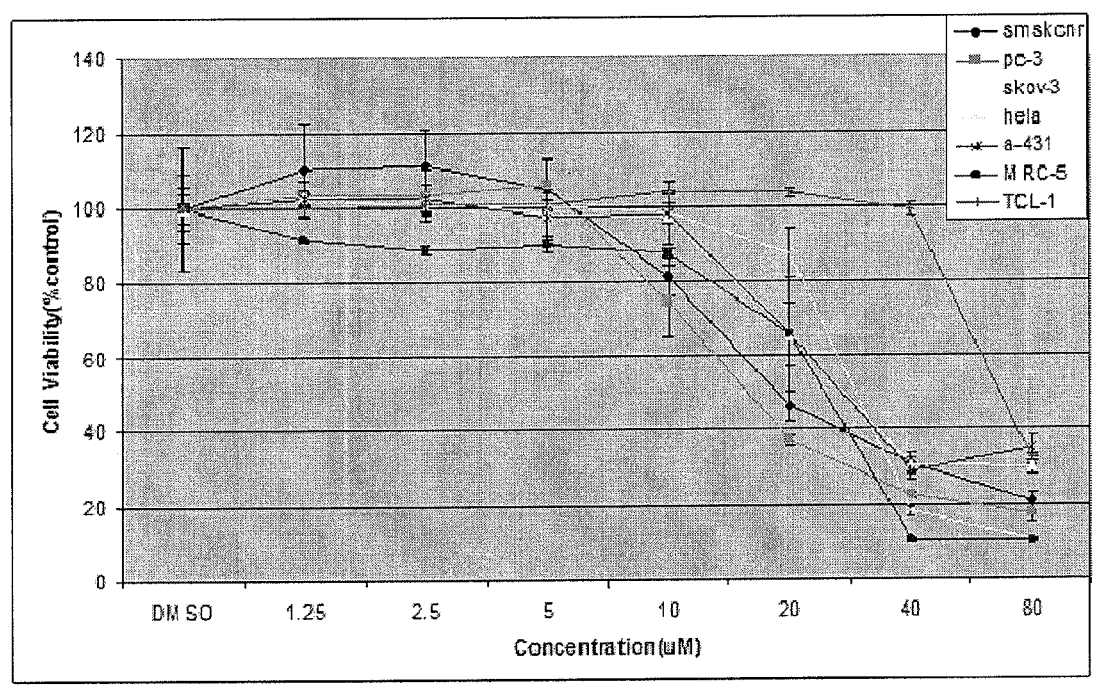
FIG. 1 depicts the effect of AMITC (2) on the viability of a panel of chemotherapy refractory cancer cells.
Figure 2:
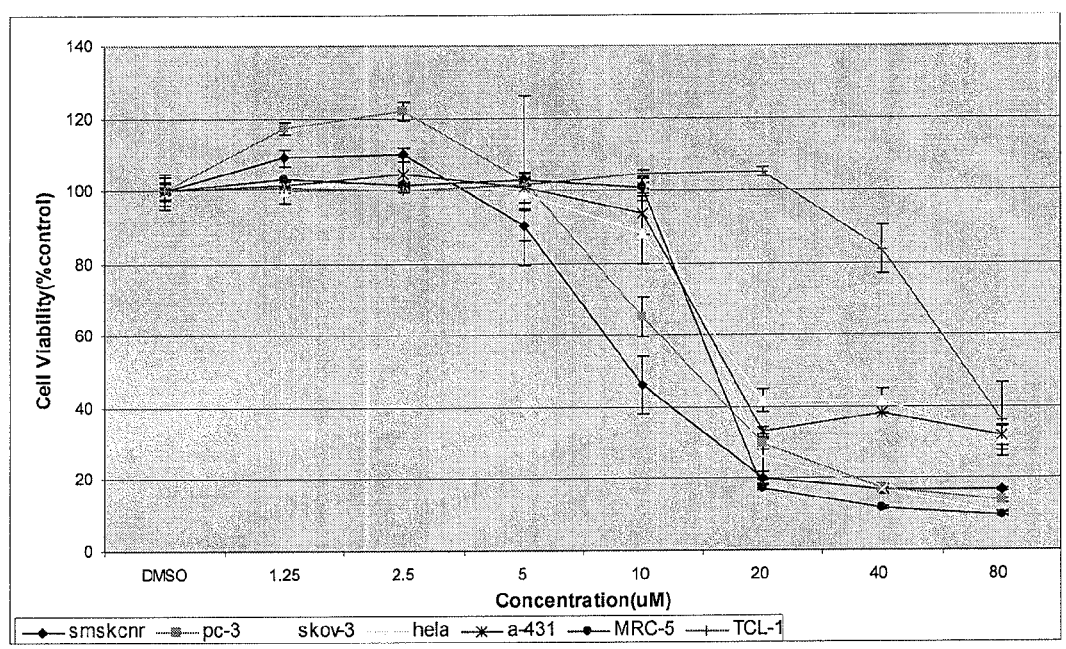
FIG. 2 depicts the effect of adamantly-N-acetylcystein (AC-AM) (3) on the viability of a panel of chemotherapy refractory cancer cells.
Figure 3:
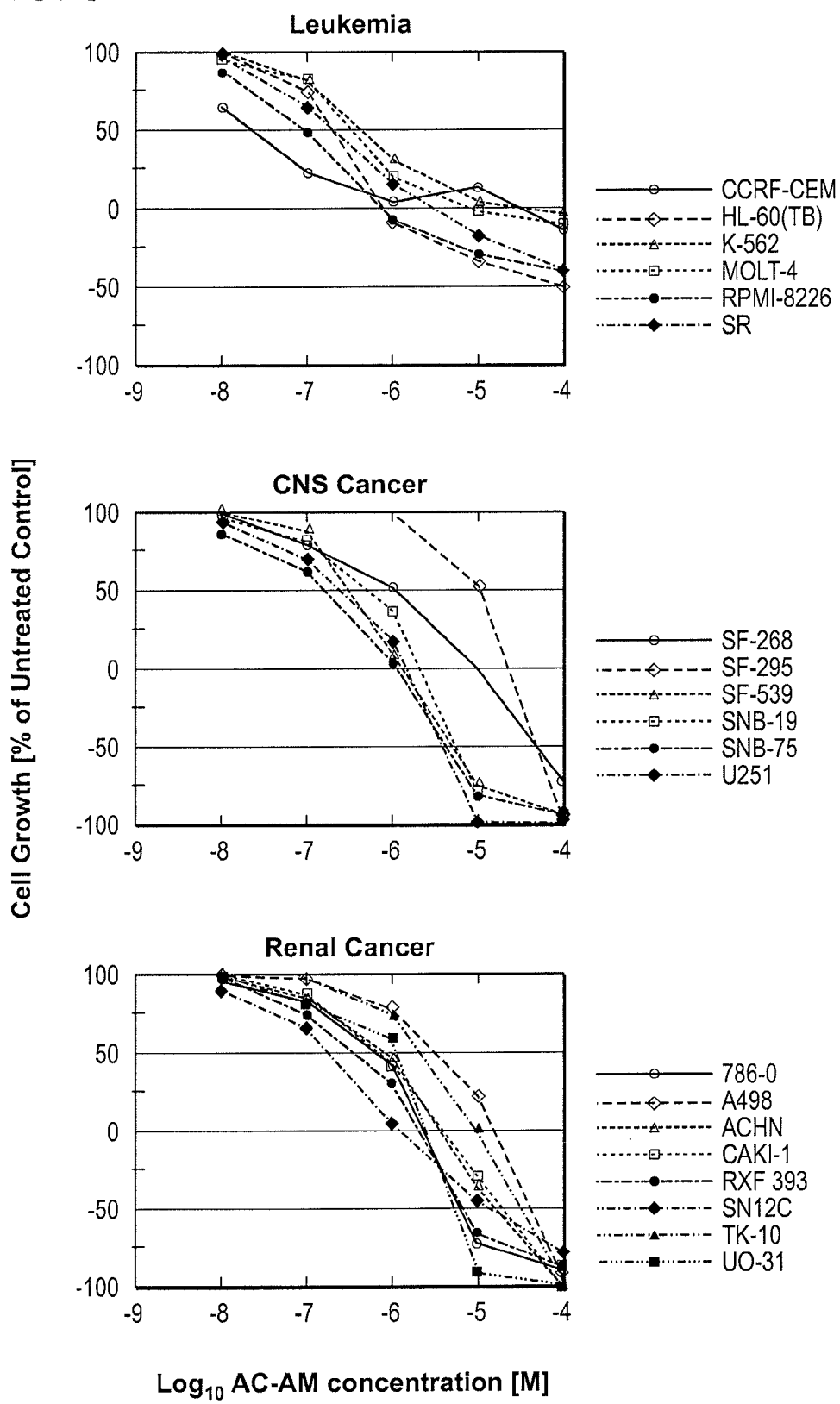
FIG. 3 depicts the effect of AC-AM on the NCI-60 cell-line panel. The outcome of in vitro growth inhibition screening of AC-AM against chemorefractory 60 cancer cell-lines included in the NCI-60 panel (http://dtp.nci.nih.gov) is shown.
Figure 3:
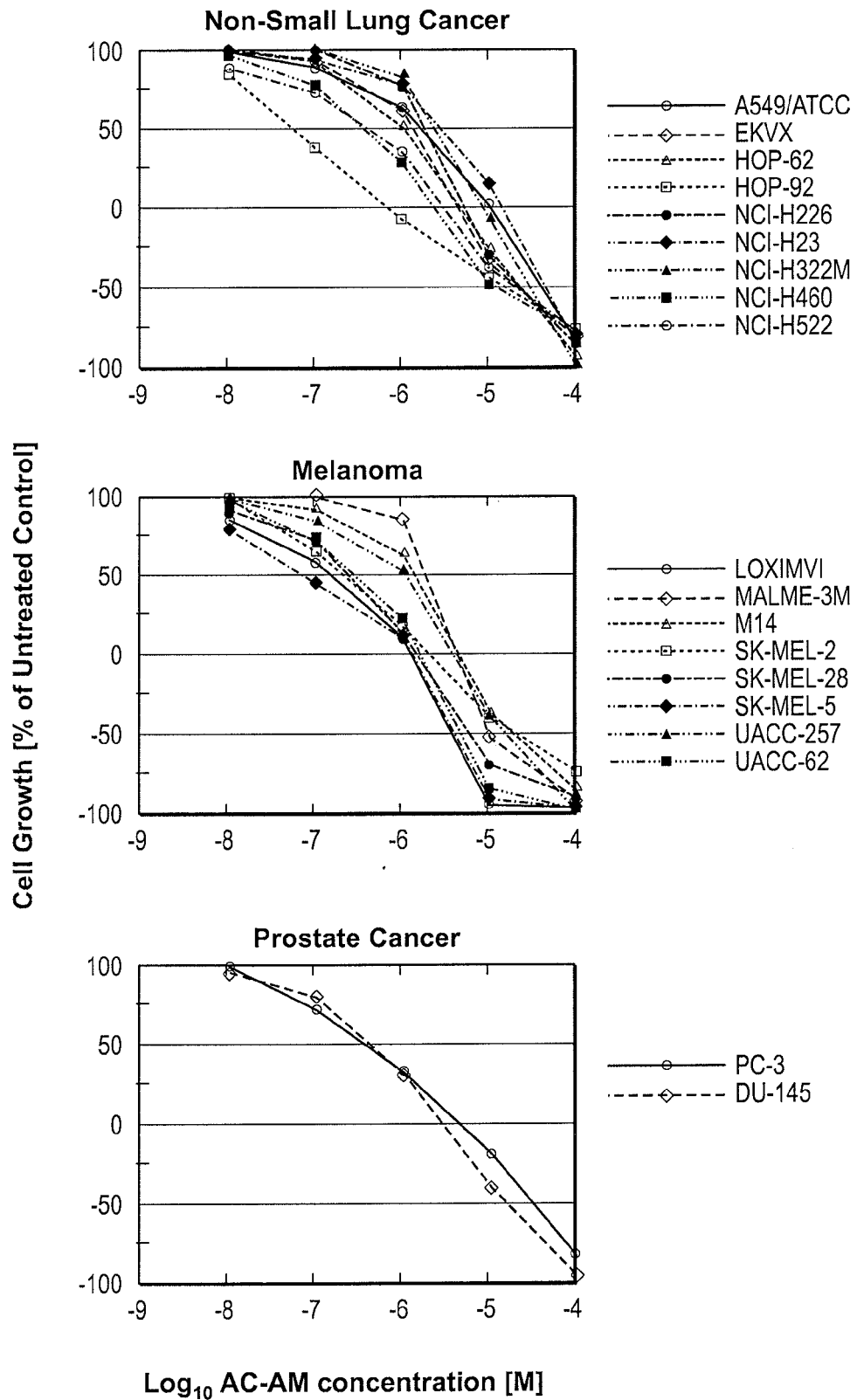
Figure 3:
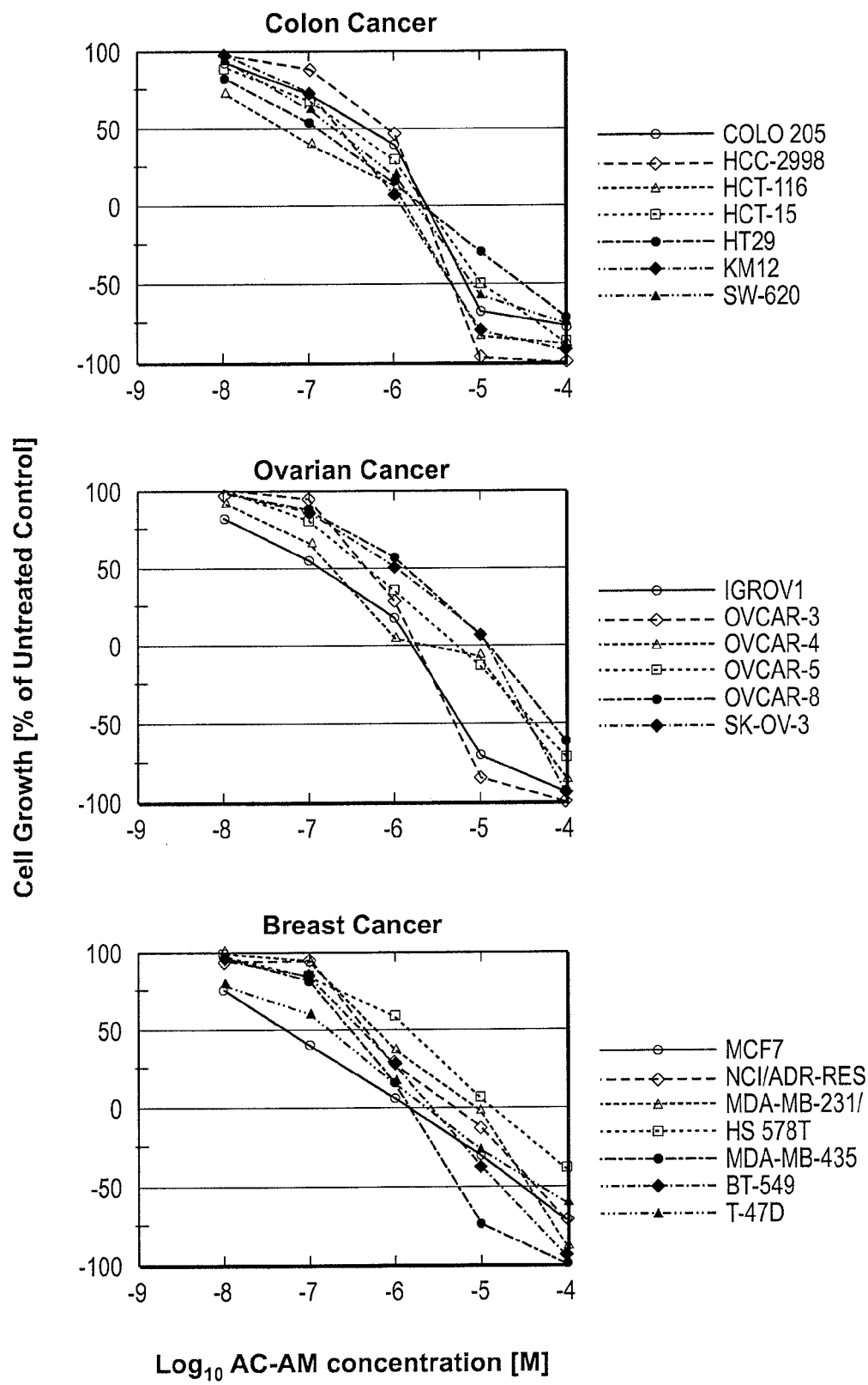
Figure 4:
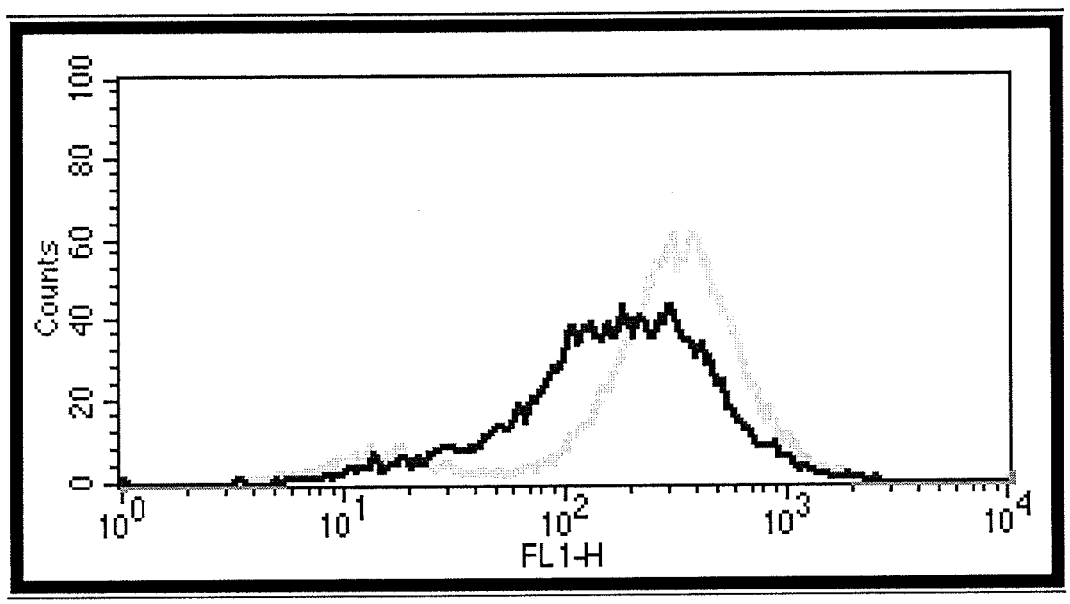
FIG. 4 depicts a majority of drug treated cells showing positive DCF staining (green/grey) as opposed to control cells (blue/black).
Figure 5:
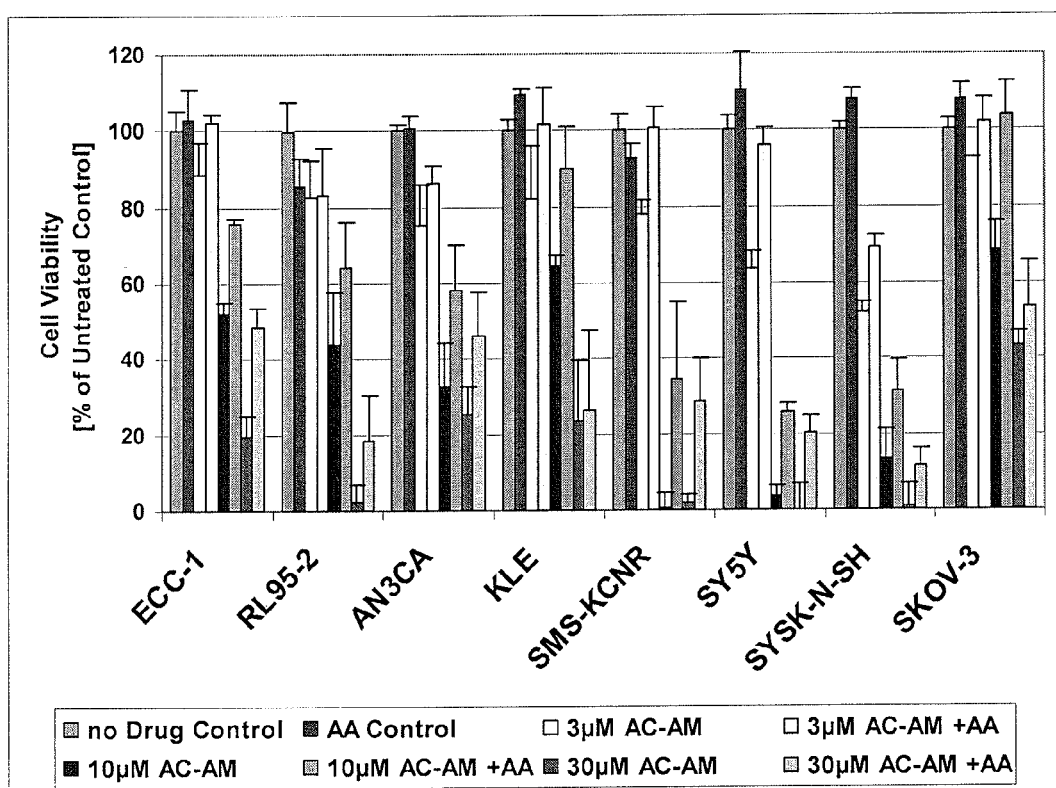
FIG. 5 depicts the role of reactive oxygen species in AC-AM mediated cytotoxicity in a panel of cancer cells in vitro.

The latest National Cancer Institute (NCI) report on cancer indicates that incidences of many solid and non solid cancers, such as non-Hodgkins lymphoma and cancers of lung, bladder and brain in women, prostate and testis in men, as well as, leukemia, myeloma, melanoma of skin, and cancers of the thyroid, kidney, pancreas, liver, neuroblastoma and esophagus is rising. Cancer treatment spending continues to rise. Unexplained cancer-related health disparities remain among population subgroups. People with low socio-economic status have the highest rates of new cancers, least treatment options and highest cancer deaths.

Isothiocyanates (ITCs) have currently been studied for its potent chemo preventive potential against chemically induced cancers (Bianchini and Vainio. *Drug Metabolism Review* 2004; 36, 655-667). ITCs are small family of organic compound that occur in wide variety of plants, many of which are consumed by humans on regular basis. ITCs are synthesized and stored in plant cells as glucosinolates (h-thioglucoside N-hydroxysulfates), then released when plant cells are injured (Fahey et al, *Phytochemistry* 2001, 56(1), 5-51). The conversion is catalyzed by myrosinase, which coexists with, but is structurally segregated from glucosinolates in intact plants. Human enteric microflora also possesses myrosinase activity and can convert a significant portion of the ingested unhydrolyzed glucosinolates to ITCs. Unlike the ITCs which are electrophilic and biologically active, the glucosinolates are chemically stable and biologically inert. More than 20 ITCs, the majority of which occur in vegetables, have been shown to inhibit tumorigenesis induced by a wide variety of chemical carcinogens in animal models, inhibiting tumorigenesis in the lung, stomach, colon, liver, esophagus, bladder, and mammary glands. Several recent epidemiological studies have suggested that humans who consumed higher levels of ITCs might be less likely to develop lung and colon cancer (Hidgon et al. *Pharmacology Research* 2007, 55, 224-236).

ITCs possess potent mechanism-based detoxification of xenobiotic carcinogens, by up-regulating phase-2 detoxification enzymes in the liver to prevent oxidative cell and DNA damage. ITCs cause the release of transcription factor Nrf2 from a cyto-skeletally bound Keapl (or inhibitory Nrf2) protein. This facilitates the translocation of Nrf2 to the nucleus where it can interact with either Jun family proteins or with small Maf proteins. The translocation of Nrf2 to the nucleus leads to the activation of AREs, whereby phase-2 proteins gene transcription and expression is promoted. Hence, ITCs appear to have therapeutic potential to manage diseases in which oxidative cell death and DNA damage appears to be the primary cause such as hypertension, atherosclerosis and cancer.

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms of "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology and virology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

All patents, patent applications and publications referred to herein are incorporated by reference in their entirety. In case of a conflict in terminology, the present specification is controlling.

As used herein, "alkyl", "$C_1$, $C_2$, $C_3$, $C_4$, $C_5$, $C_6$, $C_7$ or $C_8$ alkyl" or "$C_1$-$C_8$ alkyl" is intended to include $C_1$, $C_2$, $C_3$, $C_4$, $C_5$, $C_6$, $C_7$ or $C_8$ straight chain (linear) saturated aliphatic hydrocarbon groups and $C_3$, $C_4$, $C_5$, $C_6$, $C_7$ or $C_8$ branched saturated aliphatic hydrocarbon groups. For example, $C_1$-$C_8$ alkyl is intended to include $C_1$, $C_2$, $C_3$, $C_4$, $C_5$, $C_6$, $C_7$ and $C_8$ alkyl groups. Alkyl can also include e.g., $C_{1-6}$ alkyl, $C_{1-5}$ alkyl, $C_{1-4}$ alkyl, $C_{1-3}$ alkyl or $C_{1-2}$ alkyl. Examples of alkyl include, moieties having from one to eight carbon atoms, such as, but not limited to, methyl, ethyl, n-propyl, i-propyl, n-butyl, s-butyl, t-butyl, n-pentyl, s-pentyl, n-hexyl, n-heptyl, or n-octyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

"Heteroalkyl" groups are alkyl groups, as defined above, that have an oxygen, nitrogen, sulfur or phosphorous atom replacing one or more hydrocarbon backbone carbon atoms.

As used herein, the term "cycloalkyl", "$C_3$, $C_4$, $C_5$, $C_6$, $C_7$ or $C_8$ cycloalkyl" or "$C_3$-$C_8$ cycloalkyl" is intended to include hydrocarbon rings having from three to eight carbon atoms in their ring structure. In one embodiment, a cycloalkyl group has five or six carbons in the ring structure.

The term "substituted alkyl" refers to alkyl moieties having substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

Unless the number of carbons is otherwise specified, "lower alkyl" includes an alkyl group, as defined above, having from one to six, or, in another embodiment from one to four, carbon atoms in its backbone structure. "Lower alkenyl" and "lower alkynyl" have chain lengths of, for example, two to six or of two to four carbon atoms.

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), branched alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched alkenyl group has six or fewer carbon atoms in its backbone (e.g., $C_2$-$C_6$ for straight chain, $C_3$-$C_6$ for branched chain). Likewise, cycloalkenyl groups may have from five to eight carbon atoms in their ring structure, and in one embodiment, cycloalkenyl groups have five or six carbons in the ring structure. The term "$C_2$-$C_8$" includes alkenyl groups containing two to eight carbon atoms. The term "$C_3$-$C_8$" includes alkenyl groups containing three to eight carbon atoms.

"Heteroalkenyl" includes alkenyl groups, as defined herein, having an oxygen, nitrogen, sulfur or phosphorous atom replacing one or more hydrocarbon backbone carbons.

The term "substituted alkenyl" refers to alkenyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), branched alkynyl groups, and cycloalkyl or cycloalkenyl substituted alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_8$" includes alkynyl groups containing two to eight carbon atoms. The term "$C_3$-$C_8$" includes alkynyl groups containing three to eight carbon atoms.

"Heteroalkynyl" includes alkynyl groups, as defined herein, having an oxygen, nitrogen, sulfur or phosphorous atom replacing one or more hydrocarbon backbone carbons.

The term "substituted alkynyl" refers to alkynyl moieties having substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aryl" includes groups with aromaticity, including "conjugated", or multicyclic, systems with at least one aromatic ring. Examples include phenyl, benzyl, etc.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11-, 12-, 13- or 14-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (e.g., N or $NR_4$ wherein $R_4$ is H or other substituents, as defined). The nitrogen and sulfur heteroatoms may optionally be oxidized (i.e., N→O and $S(O)_p$, where p=1 or 2). It is to be noted that, in one embodiment, the total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthridine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted", as used herein, means that any one or more hydrogen atoms on the designated atom is replaced with a selection from the indicated groups, provided that the designated atom's normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

Combinations of substituents and/or variables are permissible, but only if such combinations result in stable compounds.

The term "hydroxy" or "hydroxyl" includes groups with an —OH or the deprotonated form, —O⁻.

As used herein, "halo" or "halogen" refers to fluoro, chloro, bromo and iodo. The term "perhalogenated" generally refers to a moiety wherein all hydrogen atoms are replaced by halogen atoms.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

"Acyl" includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, wherein oxygen, nitrogen or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

The term "ether" includes compounds or moieties which contain an oxygen atom bonded to two carbon atoms or heteroatoms. For example, the term includes "alkoxyalkyl", which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls and alkthioalkynyls. The term "alkthioalkyls" include moieties with an alkyl, alkenyl or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" includes moieties where a nitrogen atom is covalently bonded to at least one carbon or heteroatom. "Alkylamino" includes groups of compounds wherein nitrogen is bound to at least one alkyl group. Examples of alkylamino groups include benzylamino, methylamino, ethylamino, phenethylamino, etc. "Dialkylamino" includes groups wherein the nitrogen atom is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Alkylarylamino", "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

As used herein, the term "amino acid" refers to a compound comprising a primary amino (—NH2) group and a carboxylic acid (—COOH) group. The amino acids used in the present invention include naturally occurring and synthetic α, β, γ or δ amino acids, and includes but are not limited to, amino acids found in proteins. Exemplary amino acids include, but are not limited to, glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In some embodiments, the amino acid may be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-argininyl or β-histidinyl. Additionally, as used herein, "amino acids" also include derivatives of amino acids such as esters, and amides, and salts, as well as other derivatives, including derivatives having pharmacoproperties upon metabolism to an active form.

As used herein, the term "natural a amino acid" refers to a naturally occurring α-amino acid comprising a carbon atom bonded to a primary amino (—NH$_2$) group, a carboxylic acid (—COOH) group, a side chain, and a hydrogen atom. Exemplary natural a amino acids include, but are not limited to, glycine, alanine, valine, leucine, isoleucine, methionine, phenylalanine, tryptophane, proline, serine, threonine, cysteine, tyrosine, asparaginate, glutaminate, aspartate, glutamate, lysine, arginine and histidine.

As used herein, "subject", as used herein, means a mammalian subject (e.g., dog, cat, horse, cow, sheep, goat, monkey, etc.), and particularly human subjects (including both male and female subjects, and including neonatal, infant, juvenile, adolescent, adult and geriatric subjects, and further including various races and ethnicities including, but not limited to, white, black, Asian, American Indian and Hispanic.

As used herein, "treatment", "treat", and "treating" refer to reversing, alleviating, inhibiting the progress, or delaying the progression of a disorder or disease as described herein.

As used herein, "prevention", "prevent", and "preventing" describes reducing or eliminating the onset of the symptoms or complications of the disease, condition or disorder.

As used herein "an effective amount" refers to an amount that causes relief of symptoms of a disorder or disease as noted through clinical testing and evaluation, subject observation, and/or the like. An "effective amount" can further designate a dose that causes a detectable change in biological or chemical activity. The detectable changes may be detected and/or further quantified by one skilled in the art for the relevant mechanism or process. Moreover, an "effective amount" can designate an amount that maintains a desired physiological state, i.e., reduces or prevents significant decline and/or promotes improvement in the condition of interest. In some embodiments, an "effective amount" can further refer to a therapeutically effective amount.

Furthermore, it will be appreciated by one of ordinary skill in the art that the synthetic methods, as described herein, utilize a variety of protecting groups. As used herein, the term "protecting group" refers to a particular functional moiety, e.g., O, S, or N, that is temporarily blocked so that a reaction can be carried out selectively at another reactive site in a multifunctional compound. Protecting groups may be introduced and removed at appropriate stages during the synthesis of a compound using methods that are known to one of ordinary skill in the art. The protecting groups are applied according to standard methods of organic synthesis as described in the literature (Theodora W. Green and Peter G. M. Wuts (2007) *Protecting Groups in Organic Synthesis*, 4th edition, John Wiley and Sons, incorporated by reference with respect to protecting groups).

Exemplary protecting groups include, but are not limited to, oxygen, sulfur, nitrogen and carbon protecting groups. For example, oxygen protecting groups include, but are not limited to, methyl ethers, substituted methyl ethers (e.g., MOM (methoxymethyl ether), MTM (methylthiomethyl ether), BOM (benzyloxymethyl ether), PMBM (p¬imethoxybenzyloxymethyl ether), optionally substituted ethyl ethers, optionally substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), esters (e.g., formate, acetate, benzoate (Bz), trifluoroacetate, dichloroacetate) carbonates, cyclic acetals and ketals. In addition, exemplary nitrogen protecting groups include, but are not limited to, carbamates (including methyl, ethyl and substituted ethyl carbamates (e.g., Troc), amides, cyclic imide derivatives, N-Alkyl and N-Aryl amines, imine derivatives, and enamine derivatives, etc. Certain other exemplary protecting groups are detailed herein, however, it will be appreciated that the present invention is not intended to be limited to these protecting groups; rather, a variety of additional equivalent protecting groups may be utilized according to methods known to one skilled in the art.

This invention comprises of the synthesis, biological evaluations, applications and pharmaceutical compositions of the compounds provided herein. Included are analogues, methods of preparations, compositions and use. Further, this invention comprises the animal metabolites of the adamantyl derivatives described herein, their isolation, synthesis and therapeutic and other commercial usage.

The invention also comprises methods of using the compounds described herein for cancer chemotherapy or potentiation of cancer chemotherapy synergistically or additively, as de-novo drugs, including analogues thereof, possessing such therapeutic applications as antineoplastic, anti-angiogenic and other modes of anticancer activities including free radical modulation, cell-cycle progression, proapoptotic or pro-survival signaling modulation in a variety of cancer types. The present invention also provides methods of using the compounds described herein as anti-Alzheimer's, anti-arthritic, anti-fibrosis, anti-sickle cell anemic, antibacterial, antifungal, anti-thrombotics, and anti-diabetic agents. Further, the invention also comprises methods of using the compounds described herein for the treatment of auto-immune disorders, and cell-adhesion and various neurotransmitter and Nuclear receptor disorders.

In addition, this invention provides compositions and methods that are useful for chemoprevention of chemical carcinogenesis. The present invention includes pharmaceutical compositions, delivery methods in drug regimens as a single agent, or in combination with one or more additional therapeutic agents or therapeutic options in cancer treatment. Examples of such options include surgery, hormonal therapies, radiotherapies, chemotherapies derived from nature, their altered forms, synthetic ligands, targeted therapies, such as Avastin® or Iressa®, or one or more monoclonal and polyclonal antibodies that target proteins in cancer malignancies.

According to some aspects of the present invention, novel compounds with a range of biological properties are provided. Compounds described herein have biological activities relevant for the treatment of cancer.

According to one aspect of the present invention, provided herein are compounds of Formula I:

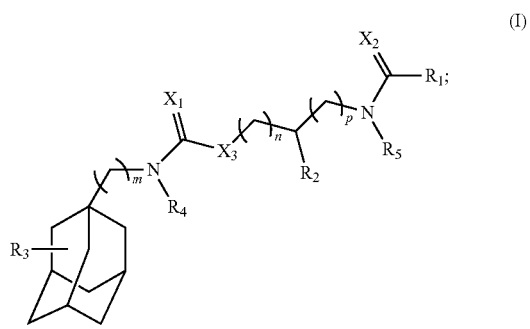

(I)

wherein $X_1$, $X_2$ and $X_3$ are each, independently, O, S, $NR_x$ or $CR_7R_{7'}$;

m, n and p are each, independently, integers from 0 to 20;

$R_1$, $R_2$ and $R_3$ are each, independently, hydrogen, nitro, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, unsubstituted or substituted $C_{2-8}$ alkynyl, hydroxyl, halogen, —$NR_{10}R_{11}$, —$C(O)R_{10}$, —$C(O)OR_{10}$, —$NR_{11}C(O)R_{10}$, —$C(O)NR_{10}R_{11}$, —$OC(O)R_{10}$, —$NR_{11}C(S)R_{10}$, or —$SO_2R_{12}$;

$R_4$ and $R_5$ are each, independently, hydrogen or unsubstituted or substituted $C_1$-$C_8$ alkyl;

$R_x$ is hydrogen, unsubstituted or substituted $C_1$-$C_8$ alkyl, or —$NR_yR_z$;

$R_y$ and $R_z$ are each, independently, hydrogen, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, or unsubstituted or substituted $C_2$-$C_8$ alkynyl;

$R_7$ and $R_{7'}$ are each, independently, hydrogen, nitro, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, unsubstituted or substituted $C_2$-$C_8$ alkynyl, hydroxyl, halogen, —$NR_8R_9$, —$C(O)R_8$, —$C(O)OR_8$, —$NR_9C(O)R_8$, —$C(O)NR_8R_9$, —$OC(O)R_8$, —$NR_9C(S)R_8$, or —$SO_2R_{15}$;

$R_8$, $R_9$, $R_{10}$ and $R_{11}$ are each, independently, hydrogen, hydroxyl, unsubstituted or substituted $C_1$-$C_8$ alkoxyl, unsubstituted or substituted $C_1$-$C_8$ alkyl, —$NR_{13}R_{13'}$ or —$NR_{14}NR_{13}R_{13'}$;

$R_{12}$ and $R_{15}$ are each, independently, halogen, hydroxyl, —$NR_{15}R_{15'}$, —$P(O)(OR_{15})_3$, CN, or —$NR_{17}NR_{16}R_{16'}$;

$R_{14}$ and $R_{17}$ are each, independently, hydrogen or unsubstituted or substituted $C_1$-$C_8$ alkyl; and $R_{13}$, $R_{13'}$, $R_{15}$, $R_{15'}$, $R_{16}$ and $R_{16'}$ are each, independently, hydrogen, hydroxyl, or unsubstituted or substituted $C_1$-$C_8$ alkyl;

or a pharmaceutically acceptable salt, prodrug, tautomer, regioisomer, stereoisomer, diastereomer, enantiomer or racemate thereof.

For example, $R_1$ is unsubstituted or substituted $C_1$-$C_8$ alkyl substituted $C_6$-$C_{14}$ aryl.

For example, $R_1$ is unsubstituted or substituted $C_6$-$C_{14}$ aryl substituted $C_1$-$C_8$ alkyl.

For example, $R_2$ is unsubstituted or substituted $C_1$-$C_8$ alkyl substituted $C_6$-$C_{14}$ aryl.

For example, $R_2$ is unsubstituted or substituted $C_6$-$C_{14}$ aryl substituted $C_1$-$C_8$ alkyl.

For example, $R_3$ is unsubstituted or substituted $C_1$-$C_8$ alkyl substituted $C_6$-$C_{14}$ aryl.

For example, $R_3$ is unsubstituted or substituted $C_6$-$C_{14}$ aryl substituted $C_1$-$C_8$ alkyl.

For example, $R_y$ is unsubstituted or substituted $C_1$-$C_8$ alkyl substituted $C_6$-$C_{14}$ aryl.

For example, $R_y$ is unsubstituted or substituted $C_6$-$C_{14}$ aryl substituted $C_1$-$C_8$ alkyl.

For example, $R_z$ is unsubstituted or substituted $C_1$-$C_8$ alkyl substituted $C_6$-$C_{14}$ aryl.

For example, $R_z$ is unsubstituted or substituted $C_6$-$C_{14}$ aryl substituted $C_1$-$C_8$ alkyl.

For example, $R_7$ is unsubstituted or substituted $C_1$-$C_8$ alkyl substituted $C_6$-$C_{14}$ aryl.

For example, $R_7$ is unsubstituted or substituted $C_6$-$C_{14}$ aryl substituted $C_1$-$C_8$ alkyl.

For example, $R_{7'}$ is unsubstituted or substituted $C_1$-$C_8$ alkyl substituted $C_6$-$C_{14}$ aryl.

For example, $R_{7'}$ is unsubstituted or substituted $C_6$-$C_{14}$ aryl substituted $C_1$-$C_8$ alkyl.

According to another aspect of the present invention, provided herein are compounds of Formula II:

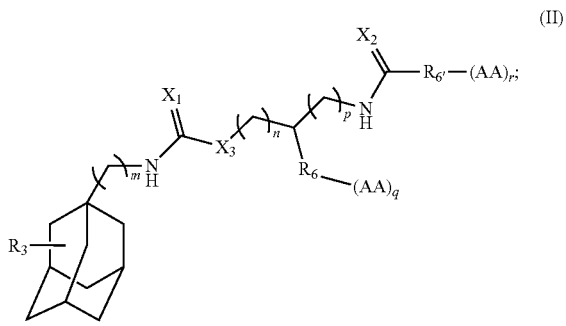

(II)

wherein $X_1$, $X_2$ and $X_3$ are each, independently, O, S, $NR_x$ or $CR_7R_{7'}$;

m, n and p are each, independently, integers from 0 to 20;

q and r are each, independently, integers from 1 to 20;

$R_3$ is hydrogen, nitro, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, unsubstituted or substituted $C_{2-8}$ alkynyl, hydroxyl, halogen, —$NR_{10}R_{11}$, —$C(O)R_{10}$, —$C(O)OR_{10}$, —$NR_{11}C(O)R_{10}$, —$C(O)NR_{10}R_{11}$, —$OC(O)R_{10}$, —$NR_{11}C(S)R_{10}$, or —$SO_2R_{12}$;

$R_6$ and $R_{6'}$ are each, independently, a bond, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, unsubstituted or substituted $C_2$-$C_8$ alkynyl, —$NR_{14}$—, —$C(O)$— or —$SO_2$—;

$R_x$ is hydrogen, unsubstituted or substituted $C_1$-$C_8$ alkyl, or —$NR_yR_z$;

$R_y$ and $R_z$ are each, independently, hydrogen, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, or unsubstituted or substituted $C_2$-$C_8$ alkynyl;

$R_7$ and $R_{7'}$ are each, independently, hydrogen, nitro, unsubstituted or substituted $C_1$-$C_8$ alkyl, unsubstituted or substituted $C_6$-$C_{14}$ aryl, unsubstituted or substituted heteroaryl comprising 1-4 heteroatoms selected from N, O and S, unsubstituted or substituted $C_2$-$C_8$ alkenyl, unsubstituted or substituted $C_2$-$C_8$ alkynyl, hydroxyl, halogen, —$NR_8R_9$, —$C(O)R_8$, —$C(O)OR_8$, —$NR_9C(O)R_8$, —$C(O)NR_8R_9$, —$OC(O)R_8$, —$NR_9C(S)R_8$, or —$SO_2R_{15}$;

$R_8$, $R_9$, $R_{10}$ and $R_{11}$ are each, independently, hydrogen, hydroxyl, unsubstituted or substituted $C_1$-$C_8$ alkoxyl, unsubstituted or substituted $C_1$-$C_8$ alkyl, —$NR_{13}R_{13'}$ or —$NR_{14}NR_{13}R_{13'}$;

$R_{12}$ and $R_{15}$ are each, independently, halogen, hydroxyl, —$NR_{15}R_{15'}$, —$P(O)(OR_{15})_3$, CN, or —$NR_{17}NR_{16}R_{16'}$;

$R_{14}$ and $R_{17}$ are each, independently, hydrogen or unsubstituted or substituted $C_1$-$C_8$ alkyl;

$R_{13}$, $R_{13'}$, $R_{15}$, $R_{15'}$, $R_{16}$ and $R_{16'}$ are each, independently, hydrogen, hydroxyl, or unsubstituted or substituted $C_1$-$C_8$ alkyl; and each AA is, independently, a substituted or unsubstituted, naturally occurring or synthetic amino acid;

or a pharmaceutically acceptable salt, prodrug, tautomer, regioisomer, stereoisomer, diastereomer, enantiomer or racemate thereof.

For example, AA is

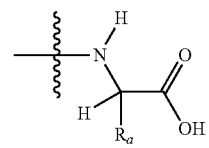

wherein $R_a$ is a side chain from a naturally occurring amino acid. In one embodiment, $R_a$ is unsubstituted or substituted $C_1$-$C_8$ alkyl.

For example, AA is an alpha-amino acid.

For example, AA is a beta-amino acid.

For example, AA is a gamma-amino acid.

For example, $(AA)_q$ or $(AA)_r$ is a peptide.

For example, $(AA)_q$ or $(AA)_r$ is a polypeptide.

For example, $(AA)_q$ or $(AA)_r$ is an azapeptide.

For example, $R_1$ is unsubstituted or substituted $C_1$-$C_8$ alkyl substituted $C_6$-$C_{14}$ aryl.

For example, $R_1$ is unsubstituted or substituted $C_6$-$C_{14}$ aryl substituted $C_1$-$C_8$ alkyl.

For example, $R_3$ is unsubstituted or substituted $C_1$-$C_8$ alkyl substituted $C_6$-$C_{14}$ aryl.

For example, $R_3$ is unsubstituted or substituted $C_6$-$C_{14}$ aryl substituted $C_1$-$C_8$ alkyl.

For example, $R_6$ is unsubstituted or substituted $C_1$-$C_8$ alkyl substituted $C_6$-$C_{14}$ aryl.

For example, $R_6$ is unsubstituted or substituted $C_6$-$C_{14}$ aryl substituted $C_1$-$C_8$ alkyl.

For example, $R_y$ is unsubstituted or substituted $C_1$-$C_8$ alkyl substituted $C_6$-$C_{14}$ aryl.

For example, $R_y$ is unsubstituted or substituted $C_6$-$C_{14}$ aryl substituted $C_1$-$C_8$ alkyl.

For example, $R_z$ is unsubstituted or substituted $C_1$-$C_8$ alkyl substituted $C_6$-$C_{14}$ aryl.

For example, $R_z$ is unsubstituted or substituted $C_6$-$C_{14}$ aryl substituted $C_1$-$C_8$ alkyl.

For example, $R_7$ is unsubstituted or substituted $C_1$-$C_8$ alkyl substituted $C_6$-$C_{14}$ aryl.

For example, $R_7$ is unsubstituted or substituted $C_6$-$C_{14}$ aryl substituted $C_1$-$C_8$ alkyl.

For example, $R_{7'}$ is unsubstituted or substituted $C_1$-$C_8$ alkyl substituted $C_6$-$C_{14}$ aryl.

For example, $R_{7'}$ is unsubstituted or substituted $C_6$-$C_{14}$ aryl substituted $C_1$-$C_8$ alkyl.

In a particular embodiment, the present invention includes one or more compounds listed in Table A or a pharmaceutically acceptable salt, prodrug, tautomer, regioisomer, stereoisomer, diastereomer, enantiomer or racemate thereof.

TABLE A

Compound a

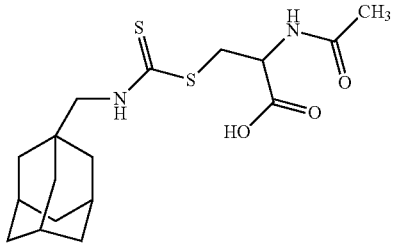 [SMILES: CC(=O)NC(CSC(=S)NCC12CC3CC(CC(C3)C1)C2)C(=O)O]

The compounds described herein may contain one or more asymmetric centers, depending upon the location and nature of the various substituents. Asymmetric carbon atoms may be present in the (R) or (S) configuration. When the orientation of a bond around a chiral center is not specified in a formula, it is to be understood that the formula encompasses every possible isomer such as geometric isomer, optical isomer, stereoisomer and tautomer based on asymmetric carbon, which can occur in the structures of the compounds described herein. In one embodiment, the compounds of the present invention are isomers with the configuration which produces the compound described herein with the more desirable biological activity. In certain embodiments, asymmetry may also be present due to restricted rotation about a given bond, for example, the central bond adjoining two aromatic rings of the specified compounds. Substituents on a ring may also be present as either cis or trans isomer and a substituent on a double bond may be present in either Z or E isomer. It is intended that all isomers (including enantiomers and diastereomers), either by nature of asymmetric centers or by restricted rotation as described above, as separated, pure or partially purified isomers or racemic mixtures thereof, be included within the scope of the present invention. The purification of said isomers and the separation of said isomeric mixtures may be accomplished by standard techniques known in the art.

As described herein, compounds of the invention may optionally be substituted with one or more substituents, such as are illustrated generally above, or as exemplified by particular classes, subclasses, and species of the invention. In general, the term "substituted" refers to the replacement of hydrogen radicals in a given structure with the radical of a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

In cases where compounds are sufficiently basic or acidic to form stable nontoxic acid or base salts, administration of the compound as a pharmaceutically acceptable salt may be appropriate. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. In particular, examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

The present invention includes salts of the compounds of Formulae I and II or Compound a.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In one embodiment, the present invention is a pharmaceutical composition comprising the compounds described herein. In another embodiment, the pharmaceutical composition further comprises a pharmaceutically acceptable carrier. The term "pharmaceutically acceptable carrier" as used herein refers to any substance, not itself a therapeutic agent, used as a vehicle for delivery of a therapeutic agent to a subject. In some embodiments, the pharmaceutical composition further comprises one or more additional therapeutically active agents against cancer.

Any suitable route of administration may be employed for providing a mammal, especially a human with an effective dosage of a compound of the present invention. For example, the compositions of the present invention may be suitable for formulation for oral, parenteral, inhalation spray, topical, rectal, nasal, sublingual, buccal, vaginal or implanted reservoir administration, etc. In some embodiments, the compositions are administered orally, topically, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

A pharmaceutically acceptable oil may be employed as a solvent or suspending medium in compositions of the present invention. Fatty acids, such as oleic acid and its glyceride derivatives are suitably included in injectable formulations, as are natural pharmaceutically acceptable oils, such as olive oil or castor oil, especially in their polyoxyethylated versions. The oil containing compositions of the present invention may also contain a long-chain alcohol diluent or dispersant, such as carboxymethyl cellulose or similar dispersing agents that are commonly used in the formulation of pharmaceutically acceptable dosage forms including emulsions and suspensions. The compositions suitably further comprise surfactants (such as non-ionic detergents including Tween® or Span®) other emulsifying agents, or bioavailability enhancers.

The compositions of this invention may be in the form of an orally acceptable dosage form including, but not limited to, capsules, tablets, suspensions or solutions. The oral dosage form may include at least one excipient. Excipients used in oral formulations of the present can include diluents, substances added to mask or counteract a disagreeable taste or odor, flavors, dyes, fragrances, and substances added to improve the appearance of the composition. Some oral dosage forms of the present invention suitably include excipients, such as disintegrants, binding agents, adhesives, wetting agents, polymers, lubricants, or glidants that permit or facilitate formation of a dose unit of the composition into a discrete article such as a capsule or tablet suitable for oral administration. Excipient-containing tablet compositions of the invention can be prepared by any suitable method of pharmacy which includes the step of bringing into association one or more excipients with a compound of the present invention in a combination of dissolved, suspended, nanoparticulate, microparticulate or controlled-release, slow-release, programmed-release, timed-release, pulse-release, sustained-release or extended-release forms thereof.

Alternatively, pharmaceutically acceptable compositions of this invention may be in the form of a suppository for rectal administration. The suppositories can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of the present invention may be in the faun of a topical solution, ointment, or cream in which the active component is suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Where the topical formulation is in the form of an ointment or cream, suitable carriers include, but are not limited to, mineral oil, sorbitan monostearate, polysorbate 60, cetyl esters wax, cetearyl alcohol, 2 octyldodecanol, benzyl alcohol and water.

The pharmaceutically acceptable compositions of this invention may also be administered by nasal, aerosol or by inhalation administration routes. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Additionally, the pharmaceutical formulation including compounds of the present invention can be in the form of a parenteral formulation. The term "parenteral" as used herein includes subcutaneous, intravenous, intramuscular, intra-articular, intra-synovial, intrasternal, intrathecal, intrahepatic, intralesional and intracranial injection or infusion techniques.

A more recently devised approach for parenteral administration employs the implantation of a slow-release or sustained-release system, such that a constant level of dosage is maintained. See, e.g., U.S. Pat. Nos. 5,629,008, 5,851,547, 6,183,461, and 3,710,795, which are incorporated herein by reference. The compounds of the present invention may be administered by transdermal patch (e.g., iontophoretic transfer) for local or systemic application.

Once detectable improvement of the subject's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Subjects can, however, require intermittent treatment on a long-term basis upon any recurrence of the disease symptoms or as a prophylactic measure to prevent disease symptom recurrence. In particular embodiments extended release formulations are contemplated.

The compounds of the present invention can also be added to extravasated blood for transfusion to inhibit oxyradical damage to the blood cells and components during storage; similarly, the compounds of the invention can also reduce oxyradical damage to blood cells in vivo.

The compounds of the present invention could also be added to rinse or storage solutions for organs and tissues, such as for organ transplantation or for surgical rinses. For example, excised organs are often placed in a preservation solution prior to transplant into a recipient. Inclusion of at least one species of a compound of the invention in a preservation solution, usually at a concentration of about 0.01 mM to 10 mM, is desirable for reducing damage due to ischemia during storage and reperfusion injury following reimplantation in the recipient.

Typically, the compound of the invention could be present in the rinse or storage solution at a concentration of about 10 μM to about 10 mM, and most usually is present at 1 mM. For example, a suitable rinse solution comprises Ringer's solution (102 mM NaCl, 4 mM KCl, 3 mM $CaCl_2$, 28 mM sodium lactate, pH 7.0) or Ringer's solution with 0.1 mM adenosine, and the compound of the invention at a final concentration of 1 mM. The rinse solution can further comprise additional antioxidants (e.g., glutathione, allopurinol). Preservation or rinse solutions containing a compound of the invention can be used to provide enhanced storage or irrigation of organs (e.g., kidney, liver, pancreas, lung, fetal neural tissue, heart, vascular grafts, bone, ligament, tendon, skin) which is believed to enhance the viability of the tissue and increase resistance to oxidative damage (e.g., as a consequence of ischemia/reperfusion).

In certain embodiments, the pharmaceutically compositions of this invention are formulated for oral administration. For oral administration to humans, the dosage range is 0.01 to 1000 mg/kg body weight in divided doses. In one embodiment the dosage range is 0.1 to 100 mg/kg body weight in divided doses. In another embodiment the dosage range is 0.5 to 20 mg/kg body weight in divided doses. For oral administration, the compositions may be provided in the form of tablets or capsules containing 1.0 to 1000 milligrams of the active ingredient, particularly, 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated.

It should also be understood that a specific dosage and treatment regimen for any particular subject will depend upon a variety of factors, including the activity of the specific compound employed, the mode of administration, the age, body weight, general health, gender, diet, rate of excretion, drug combination, and the judgment of the treating physician, the condition being treated and the severity of the condition. Such dosage may be ascertained readily by a person skilled in the art. This dosage regimen may be adjusted to provide the optimal therapeutic response.

In general, for treatment of neoplastic diseases, a suitable effective dose of a compound of the invention will be in the range of 0.01 to 1000 milligram (mg) per kilogram (kg) of body weight of recipient per day, preferably in the range of 1 to 100 mg per kg of body weight per day. The desired dosage is preferably presented in one, two, three, four or more subdoses administered at appropriate intervals throughout the day. These subdoses can be administered as unit dosage forms, for example, containing 0.5 to 10,000 mg, preferably 10 to 1000 mg of active ingredient per unit dosage form.

For example, single dosages can range from about 5 mg to about 5 g. In another embodiment, dosages are about 0.01 to about 1000 mg per kg of body weight of subject per day. In another embodiment, dosages are about 2 to about 20 mg per kg of body weight of subject per day.

Compounds of the present invention may optionally be administered in conjunction with one or more additional active compounds and/or agents useful in the treatment of viral infections as described herein. The additional compound(s) may optionally be administered concurrently. As used herein, the word "concurrently" means sufficiently close in time to produce a combined effect (that is, concurrently may be simultaneously, or it may be two or more events occurring within a short time period before or after each other).

Another aspect of the present invention provides methods of preventing or treating cancer in a subject. In some embodiments, the present invention provides methods of preventing or treating neuroblastoma, ovarian cancer, breast cancer, or cervical cancer. The methods comprise administering a subject a therapeutically effective amount of a compound described herein.

According to this invention, a therapeutically or pharmaceutically effective amount of a compound of the invention is administered to a subject to treat or prevent neoplastic disease, such as cancer. In particular embodiments, a compound of the invention is used to therapeutically treat neuroblastoma, lymphoma, leukemia, pancreatic, breast, ovarian, prostate, endometrial, cervical or colorectal cancer.

The present invention includes a method of treating subjects who have a neoplasticity associated disease with a prophylactically effective or therapeutically effective amount of a compound of Formula I or II. This method can be used to treat subjects at various stages of their diseases or to prevent development of such diseases. In addition, the treatment can be administered to prevent or reduce, the age-adjusted probability of developing a neoplasm and/or the age-adjusted mortality rate and/or the rate of senescence.

The compounds of the invention can also be administered to subjects who are infected with a human immunodeficiency virus (e.g., HIV-1) or who are at risk of becoming infected with a human immunodeficiency virus. The compounds described herein may prevent or inhibit the induction of HIV-1 replication in CD4+ lymphocytes by tumor necrosis factor (TNF) and/or prevent damage to or death of CD4+ cells as a consequence of HIV-1 infection. Without wishing to be bound by any particular theory of HIV-1 replication or HIV-1 pathogenesis, it is believed that administration of a compound described herein may inhibit and/or slow the development of HIV-1 related pathology and/or reduce the rate of decline of the CD4+ lymphocyte population in HIV-infected individuals. The compounds of the invention also may inhibit pathology resulting from excessive or inappropriate levels of TNF, both in AIDS and in other conditions (e.g., septic shock). Frequently, a dosage of about 0.005 to 5000 mg will be administered to a subject with HIV and/or with excessive or inappropriate levels of TNF, either in single or multiple doses, to reduce or retard the development of pathology and clinical symptoms. Compounds of the invention can be administered therapeutically to treat viral diseases other than HIV.

The required dosage will depend upon the nature of the disease, the severity and course of the disease, previous therapy, the subject's health status, response to the compound administered and the judgment of the treating medical caregiver. Typically, at least one compound of Formula I or II is administered as the sole active ingredient, or in combination with one or more other active ingredients, typically selected from the group consisting of N-2-mercaptopropionylglycine, N-acetylcysteine, glutathione, dimethyl thiourea, desferrioxamine, mannitol, α-tocopherol, ascorbate, buthionine sulfoximine, allopurinol, 21-aminosteroids, calpain inhibitors, glutamate receptor antagonists, tissue plasminogen activator, streptokinase, urokinase, nonsteroidal anti-inflammatory agent, cortisone, and carotenoids. Compounds of formula I or II may also be administered in conjunction with polypeptides having SOD and/or catalase activity.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, prodrug, metabolite, polymorph or solvate thereof, is more effective than combination therapy in inducing a desired biological effect.

As used herein, "combination therapy" or "co-therapy" includes the administration of a compound of the present invention, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, analog or derivative thereof, may be administered in combination with a second antiviral compound. For example, as noted above, the compositions of the present invention may include the compounds as described above in combination with one or more (e.g., 1, 2, 3) additional active agents such as described in this section in analogous manner as known in the art.

The process to be utilized in the preparation of the compounds described herein depends upon the specific compound desired. Such factors as the selection of the specific substituent and various possible locations of the specific substituent all play a role in the path to be followed in the preparation of the specific compounds of this invention. Those factors are readily recognized by one of ordinary skill in the art.

In general, the compounds of this invention may be prepared by standard techniques known in the art and by known processes analogous thereto. General methods for preparing compounds of the present invention are set forth below. In certain cases, a particular compound is described by way of example as presented further below in the section describing the examples.

In the following description, all variables are, unless otherwise noted, as defined in the formulas described herein. The following non-limiting descriptions illustrate the general methodologies that may be used to obtain the compounds described herein.

Compounds of the present invention can be synthesized according to the schemes and Examples described herein.

The present invention will now be described in more detail with reference to the following examples. However, these examples are given for the purpose of illustration and are not to be construed as limiting the scope of the invention.

Example 1

Synthesis

Compounds of the invention were synthesized according to the scheme described below.

Step a—Synthesis of adamantyl methyl isothiocyanate (2) (Adamantyl MITC)

Adamantyl methyl amine (1) was dissolved in the mixture of ethyl acetate and water (1:1) and stirred at 0° C. to 5° C. To the reaction mixture, thiophosgene (1.25 eq) was added dropwise in a well ventilated fume hood. The reaction mixture stirred at 0° C. to 5° C. temperature for 30 minutes, and thin layer chromatography (TLC) indicated complete conversion. The reaction mixture was transferred to a separatory funnel and organic layer collected, dried over anhydrous sodium sulphate and concentrated under reduced pressure to afford a semi solid which soon solidified to afford (2) as an off-white solid. (2) was characterized by Mass spectrometry: MS=208 $(M+H)^+$.

Step b—Synthesis of cysteinyl derivative (3) (AC-AM)

To the solution of (2) mixture of $H_2O$ and ethanol was added commercially available N-acetyl cysteine (1.25 eq) and the reaction mixture stirred up to 96 hrs at room temperature, in the presence of sodium bicarbonate. The ethanol was removed under reduced pressure and the residue was extracted with ethyl acetate (2×25 mL), the pH was lowered by dropwise addition of HCl (2N) until the solution turned milky white. The reaction mixture was extracted with ethyl acetate (3×25 mL). The organic layer pooled together, was dried over anhydrous sodium sulphate and concentrated under reduced pressure to afford cysteinyl derivative (3). $^1H$ NMR ($CDCl_3$): 7.7571 (bs, 1H, NH), 7.61 (bs, 1H, NH), 4.64 (bs, 1H, CH), 3.94-3.83 (d, 2H, $NCH_2$), 3.52-3.47 (d, 2H, SCH2), 2.15-1.54 (m, 20H).

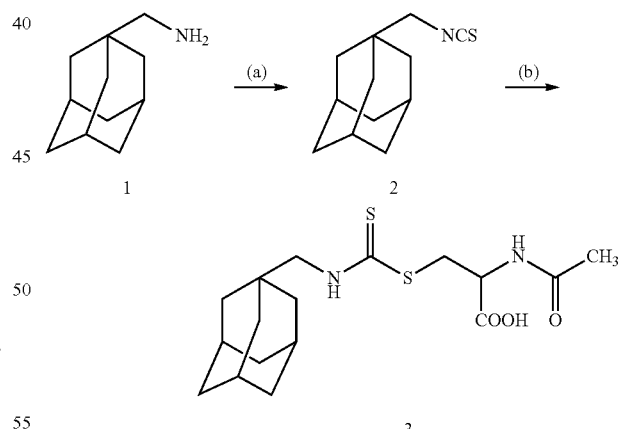

Reagents and Conditions: (a) thiophosgene, $NaHCO_3$ (10% aq), ethyl acetate, 30 min, 0° C.; (b) N-acetyl cysteine, ethanol+$H_2O$, pH=7-10, up to 96 hrs.

Example 2

Cytotoxicity of (2) and (3) Against a Panel of Cancer Cell-Lines (Including NCI60 Cell-Line Panel)

Cancer cells derived from neuroblastoma (SMSKCNR), ovarian (SKOV-3), prostate (PC-3), cervical (HeLa), skin (a431), immortalized lung fibroblasts (MRCS) and immortalized trophoblasts (TCL-1) were seeded (5000-10000) in a 96 well plate in complete medium as recommended by ATCC and allowed to adhere overnight. Medium was replaced with fresh complete medium containing various concentrations of compound (2) and (3). The cells were incubated under standard humidified incubator (5% $CO_2$) for 48 hours. The medium was replaced again with 100 µL of complete RPMI medium containing MTS reagent (Cell titre 96 aqueous one solution cell proliferation assay, Promega, Madison, Wis.) and incubated for 1-6 hours until violet farmazon color developed (the optical density (OD) of the color was read with an ELISA plate reader at 492 nm wavelength). The OD values of the treatment wells were plotted against vehicle OD as 100% cell viablity using MS excel software.

Example 3

AC-AM Treatment Caused Production of Reactive Oxygen Species (ROS) in Platinum Refractory Ovarian Cancer Cells SKOV-3 (1 million) cells were seeded in 100 mm3 petri dishes in DMEM media supplemented with 10% fetal bovine serum (FBS) and 1% antibiotic. The cells were incubated with treated with 10 µM of AC-AM and incubated for 24 hrs. The media was removed, cells were trypsinized, collected by centrifugation. The cells were incubated with DCF dye (10 µM) for 30 min and the cell population was analyzed by a FACS machine. The majority of the drug treated cells showed positive DCF staining (green/grey) as opposed to control cells (blue/black).

Example 4

The Role of Reactive Oxygen Species in AC-AM Mediated Cytotoxicity in a Panel of Cancer Cells Cancer cells derived from neuroblastoma (SMSKCNR), ovarian (SKOV-3), prostate (PC-3), endometrial (ECC-1, AN3CA, KLE), breast (MCF-7) and trophoblasts (TCL-1) were seeded (5000-10000 cells/well) in a 96 well plate in complete medium as recommended by ATCC and allowed to adhere overnight. The medium was replaced with fresh complete medium containing ascorbic acid (500 µM) and added various concentrations of AC-AM. The cells were incubated under standard humidified incubator (5% $CO_2$) for 24 hours. The medium was replaced again with 100 µL of complete RPMI medium containing MTS reagent (Cell titre 96 aqueous one solution cell proliferation assay, Promega, Madison, Wis.) and incubated for 1-6 hours until violet farmazon color developed (the optical density of the color was read with an ELISA plate reader at 492 nm wavelength). The OD values of the treatment wells were plotted against vehicle OD set at 100% cell viability using MS excel software.

Example 5

Effect of AMITC and AC-AM on the Cell Cycle Progression of SKOV-3 Cells

Figure 6:
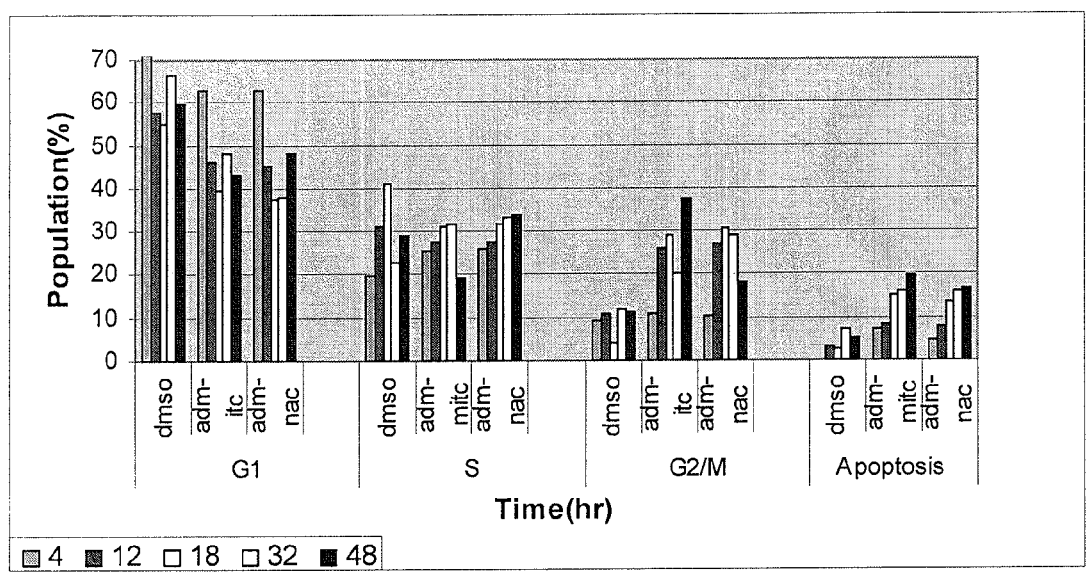
FIG. 6 depicts the effect of AMITC and AC-AM on the cell cycle progression of SKOV-3 cells.
Figure 7:
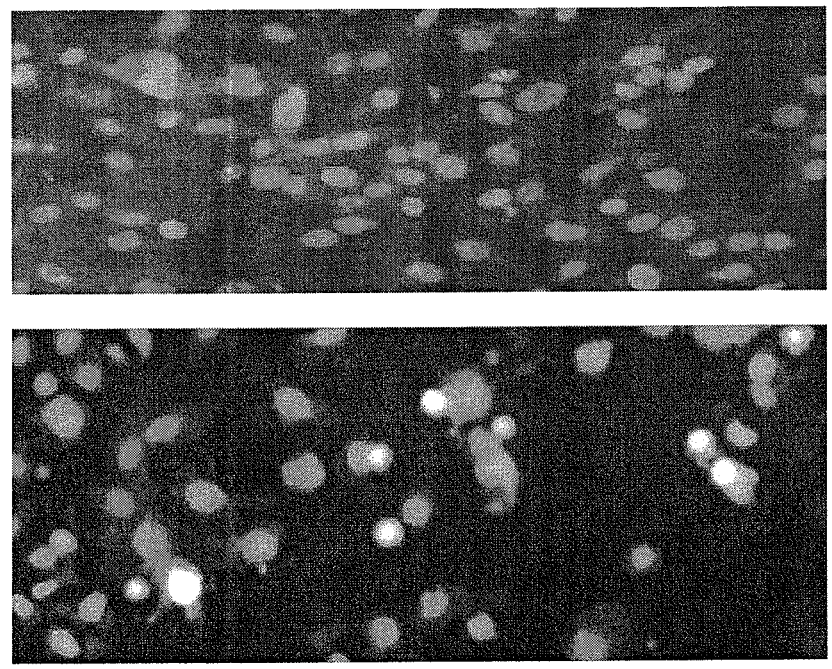
FIG. 7 depicts a TUNEL assay to visualize AC-AM induced apoptosis in SKOV-3 cells. AC-AM causes DNA nicks in the treated SKOV-3 cells within 24 hours (upper panel vehicle treated control, lower panel AC-AM treated SKOV-3 cells). Yellow colored nicks are present in the treatment group (lower panel), and absent in the control group (upper panel).

SKOV-3 cells (~1 million) were seeded in complete DMEM media in 10 $cm^2$ dishes and allowed to adhere overnight. Media was removed and supplemented with AMITC and AC-AM (10 µM) or vehicle and cells were harvested at 4, 12, 18, 32, and 48 hours. The cells were washed and fixed with cold 70% ethanol/$H_2O$. After 1 hour, ethanol was removed and 500 µL of propidinium iodide (PI) (1 mg/10 mL) was added to each tube containing cells. The distribution of the cell population in various phases of cell-cycle was analyzed using FACS. 10,000 events were chosen from each sample. As shown in Table 1 and FIG. 6, AC-AM treatment resulted in the accumulation of the cells in G2/M phase while G1 phase population steadily decreased. AC-AM treatment also resulted in an increase of sub-G1 population, which is generally considered apoptotic in nature.

TABLE 1

| Drug | Concentration | Time (hr) | G1 | S | G2/M | Apoptosis |
|---|---|---|---|---|---|---|
| DMSO | 2 µl | 4 | 71.35 | 19.52 | 9.13 | 0.08 |
| | | 12 | 57.80 | 31.36 | 10.84 | 3.21 |
| | | 18 | 55.06 | 40.91 | 4.02 | 2.62 |
| | | 32 | 66.35 | 22.61 | 11.87 | 7.35 |
| | | 48 | 59.81 | 28.82 | 11.37 | 5.37 |
| AMITC | 10 µM | 4 | 63 | 25.30 | 11 | 7.24 |
| | | 12 | 46.18 | 27.27 | 26.06 | 8.52 |
| | | 18 | 39.19 | 31.32 | 29.13 | 14.83 |
| | | 32 | 48 | 31.86 | 20.12 | 16.07 |
| | | 48 | 43 | 19.36 | 37.44 | 19.46 |
| AC-AM | 10 µM | 4 | 63 | 25.70 | 10.40 | 4.81 |
| | | 12 | 45.15 | 27.67 | 27.17 | 7.73 |
| | | 18 | 37.37 | 31.78 | 30.85 | 13.33 |
| | | 32 | 37.78 | 33.34 | 28.89 | 16.29 |
| | | 48 | 48.48 | 33.62 | 17.90 | 16.62 |

Example 6

The Role of MAP Kinases in AC-AM Induced Cell Death

Figure 8:
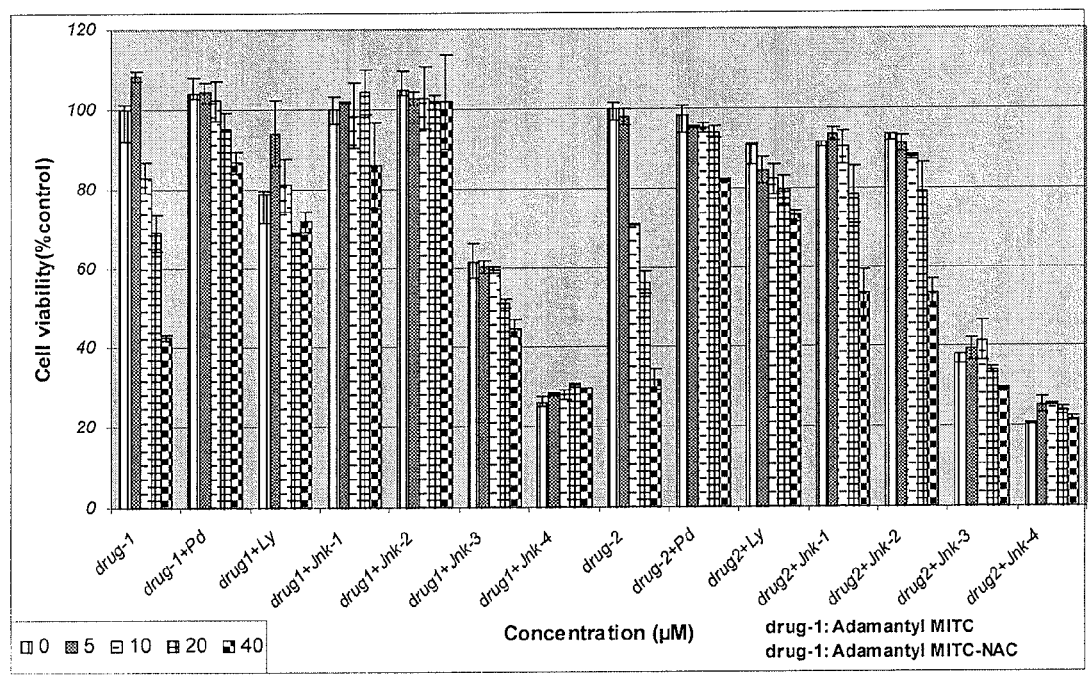
FIG. 8 depicts the role of MAP kinases in AC-AM induced cell death.

To show that AC-AM (Adamantyl MITC-NAC) mediated its cytotoxicity through MAP kinases activation, ovarian cancer (SKOV-3) cells (5000/well) were seeded in a 96 well plate in complete DMEM medium and allowed to adhere overnight. The medium was replaced with fresh complete medium containing various MAPK or SAPK/JNK inhibitors (40 µM) dissolved in 50 µL of medium and incubated for 30 minutes. Varying concentrations of AC-AM (in 50 µL of media) were then added and the cells were incubated under standard humidified incubator (5% $CO_2$) for 48 hours. The medium was replaced again with 100 µL of complete RPMI medium containing MTS reagent (1 mL/15 mL RPMI medium; Cell titre 96 aqueous one solution cell proliferation assay, Promega, Madison, Wis.) and incubated for 1-6 hours till violet farmazon color developed (the optical density of the color was read with an ELISA plate reader at 492 nm wavelength). The OD values of the treatment wells were plotted against vehicle OD set at 100% cell viability using MS excel software (FIG. 8). Pretreatment with MAP kinase inhibitors rescued the cell from undergoing apoptosis to varying degree.

Example 7

The Role of Caspases in the Cytotoxicity Induced by AC-AM

Figure 9:
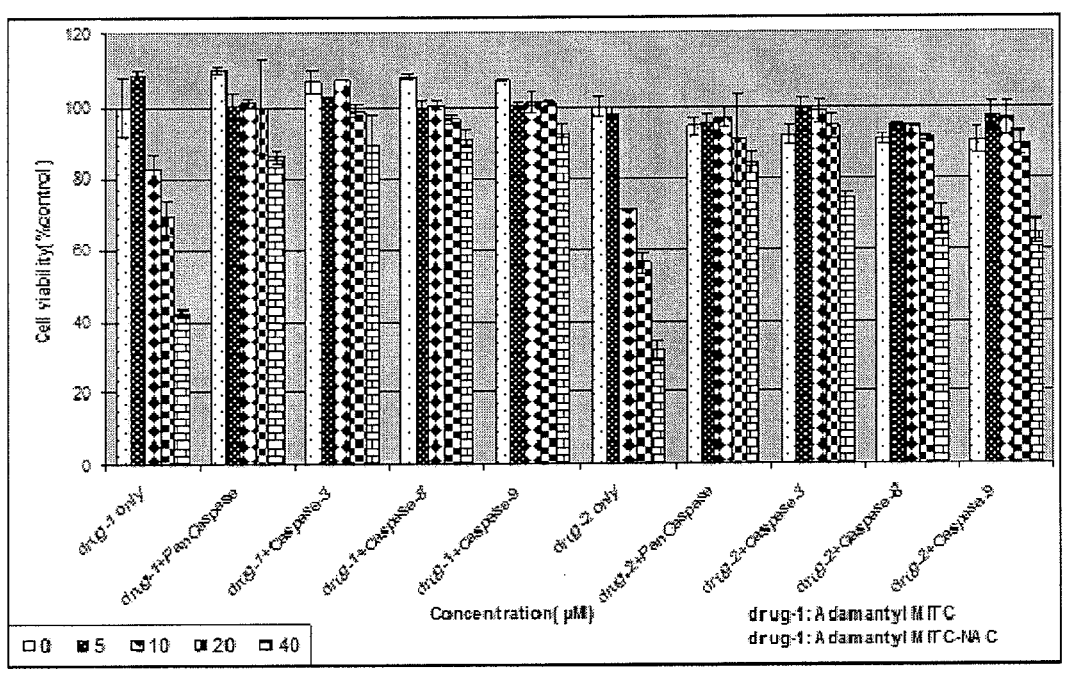
FIG. 9 depicts the role of caspases in the cytotoxicity induced by AC-AM.
Figure 10:
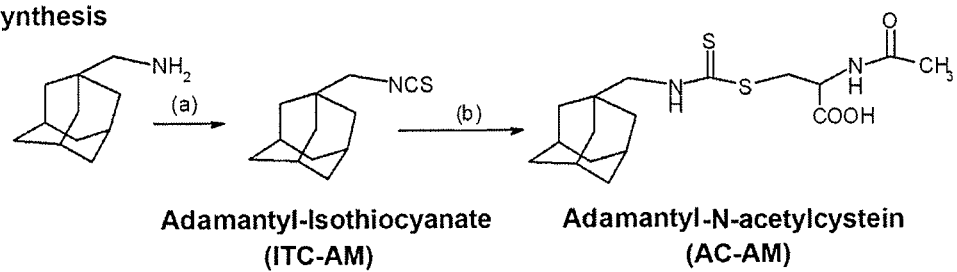
FIG. 10 (A) depicts the synthesis of AC-AM, which is generated from adamantyl and adamantyl isothiocyanate (ITC-AM or AM-ITC) as intermediate.
Figure 10:
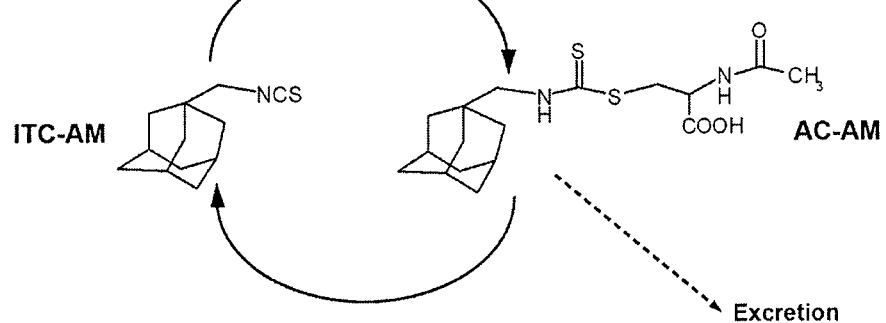

To show that AC-AM (Adamantyl MITC-NAC) mediated its cytotoxicity through caspase activation, ovarian cancer (SKOV-3) cells (5000/well) were seeded in a 96 well plate in complete DMEM medium and allowed to adhere overnight. Medium was replaced with fresh complete medium containing pancaspase, caspase-3, caspase-8 and caspase-8 inhibitors (40 µM) dissolved in 50 µL of medium and incubated for 30 minutes. Varying concentrations of AC-AM (in 50 µL of media) were then added and the cells were incubated under standard humidified incubator (5% $CO_2$) for 48 hours. The medium was replaced again with 100 μL of complete RPMI medium containing MTS reagent (Cell titre 96 aqueous one solution cell proliferation assay, Promega, Madison, Wis.) and incubated for 1-6 hours until violet farmazon color developed (the optical density of the color was read with an ELISA plate reader at 492 nm wavelength). The OD values of the treatment wells were plotted against vehicle OD set at 100% cell viability using MS excel software (FIG. 9). Pretreatment with caspase-3 inhibitors rescued the cell from undergoing apoptosis to a varying degree.

Cytotoxic Properties of Adamantyl

Example 8

Isothiocyanate and In Vivo Metabolite Adamantyl-N-Acetylcystein in Gynecological Cancer Cells Adamantyl isothiocyanate and adamantyl-N-acetylcystein are cytotoxic to cancer cells including gynecological tumor cells. Cell cycle arrest was observed after treatment of ovarian cancer cells with AC-AM in comparison with ITC-AM. The cell cycle studies revealed that adamantyl-N-acetylcystein and adamantyl isothiocyanate arrest ovarian cancer cells in G2/M phase. DNA fragmentation and induction of apoptosis was seen in ovarian cancer cells after AC-AM treatment. By TUNEL, immunoblotting, and viability studies employing caspase and p38 mitogen-activated protein kinase inhibitors, reduction in ovarian cancer cell viability was found to be a consequence of DNA fragmentation and apoptosis. Generation of intracellular ROS by AC-AM was seen in ovarian and endometrial cancer cells and cytotoxicity was blocked by antioxidant ascorbic acid. Cytotoxic action of adamantyl-N-acetylcystein in ovarian cancer cells and endometrial cancer cells required excess generation of reactive oxygen species which could thus be blocked by antioxidant co-treatment. Adamantyl-N-acetylcystein treatment led to modified expression or activation of apoptotic and oncogenic proteins such as JNK/SAPK, AKT, XIAP, and EGF-R for ovarian cancer cells and JNK/SAPK and ERK1/2 for endometrial cells. Optionally, cancer cells can be sensitized to the drug using signaling inhibitors or redox-modulating agents.

The data described herein revealed that both ITC-AM and AC-AM diminished the viability of various types of tumor cells at drug concentrations ≥10 μM. In contrast, the viability of immortalized TCL-1 trophoblasts that possess a high metabolism and growth rate similar to most cancer cells and served as controls was not significantly affected even at drug concentrations of 40 μM. Adamantyl-N-acetylcystein-induced cell death is mediated by a variety of pro-apoptotic factors including caspases.

The findings indicate that AC-AM is useful to treat (inhibit the growth or kill) various gynecological cancers. In vivo conversion between N-acetylcystein derivative AC-AM and isothiocyanate ITC-AM is likely to amplify the cytotoxic effect of this newly designed compound. Sensitivity of cancer cells to the drug is optionally modified by sensitizing target cells to the drug using inhibitors of pro-survival or growth factor (e.g., epidermal growth factor (EGF))-signaling or redox-modulating agents.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method for treating ovarian cancer or endometrial cancer in a subject in need of such treatment, the method comprising administering to said subject a therapeutically effective amount of a compound, wherein the compound comprises:

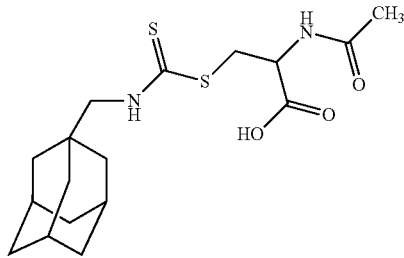 [SMILES: CC(=O)NC(CSC(=S)NCC12CC3CC(CC(C3)C1)C2)C(=O)O]

or a pharmaceutically acceptable salt, prodrug, tautomer, regioisomer, stereoisomer, diastereomer, enantiomer or racemate thereof.

2. The method of claim 1, further comprising administering to said subject an inhibitor of epidermal growth factor (EGF).

* * * * *